United States Patent
Murata et al.

(10) Patent No.: US 6,581,442 B1
(45) Date of Patent: Jun. 24, 2003

(54) SPLITTED TUBING APPARATUS FOR GRADIENT HIGH PERFORMANCE LIQUID CHROMATOGRAPHY

(75) Inventors: Kaoru Murata, Ibaraki (JP); Yasushi Ishihama, Ibaraki (JP); Nariyasu Mano, Miyagi (JP); Naoki Asakawa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/979,116

(22) PCT Filed: May 12, 2000

(86) PCT No.: PCT/JP00/03057

§ 371 (c)(1),
(2), (4) Date: Nov. 19, 2001

(87) PCT Pub. No.: WO00/72001

PCT Pub. Date: Nov. 30, 2000

(30) Foreign Application Priority Data

May 19, 1999 (JP) ............................................ 11-138854

(51) Int. Cl.[7] ............................ G01N 1/00; B01D 15/08
(52) U.S. Cl. .................................. 73/61.56; 210/198.2
(58) Field of Search ............................ 73/61.56, 61.59, 73/61.55; 422/70; 210/198.2, 656

(56) References Cited

U.S. PATENT DOCUMENTS

| | | | | |
|---|---|---|---|---|
| 3,373,872 A | * | 3/1968 | Hrdina | 210/198.2 |
| 4,506,987 A | * | 3/1985 | Daughton et al. | 366/160.3 |
| 4,954,253 A | * | 9/1990 | Alexandrov et al. | 210/198.2 |
| 5,071,562 A | * | 12/1991 | Allington et al. | 210/656 |
| 5,158,675 A | * | 10/1992 | Allington et al. | 210/198.2 |
| 5,234,587 A | * | 8/1993 | Allington et al. | 210/198.2 |
| 5,360,320 A | * | 11/1994 | Jameson et al. | 417/4 |
| 6,048,496 A | * | 4/2000 | Zhou et al. | 422/70 |

FOREIGN PATENT DOCUMENTS

| | | |
|---|---|---|
| JP | 62-95727 | 6/1987 |
| JP | A5-302916 | 11/1993 |
| JP | 5-302916 | 11/1993 |
| JP | 9-325239 | 12/1997 |
| JP | A9-325239 | 12/1997 |

OTHER PUBLICATIONS

Microfilm of the specification and drawings annexed to the request of Japanese Utility Model Application No. 188460/1985 (Laid–Open No. 95727/1987).
Wilm et al., Analytical Chemistry, vol. 68, No. 1, pp. 1–8, (1996).
Huang et al., Anal. Chem. vol. 63, pp. 732–739, (1991).
Ducret et al., Anal. Biochemistry, vol. 265, pp. 129–138, (1998).
Henzel et al., Anal. Biochemistry, vol. 187, pp. 228–233, (1990).
Chervet et al., Anal. Chem., vol. 68, pp. 1507–1512, (1996).
Takeuchi et al., J. of Chromatography, vol. 253, pp. 41–47, (1982).
Macnair et al., Rapid Comm. In Mass Spectrometry, vol. 11, pp. 1279–1285, (1997).

* cited by examiner

Primary Examiner—Helen Kwok
Assistant Examiner—J L Politzer
(74) Attorney, Agent, or Firm—Birch, Stewart, Kolasch & Birch, LLP

(57) ABSTRACT

The present invention provides a device capable of simply formulating an arbitrary gradient pattern in a low flow gradient high performance liquid chromatography. That is, the present invention provides a split tubing apparatus for a gradient high performance liquid chromatography, which comprises a solvent inlet part, a split tubing part split into two or more plural tubes, and a solvent outlet part.

16 Claims, 5 Drawing Sheets

SPLITTED TUBING APPARATUS FOR GRADIENT HIGH PERFORMANCE LIQUID CHROMATOGRAPHY

This application is the national phase under 35 U.S.C. §371 of PCT International Application No. PCT/JP00/03057 which has an International filing date of May 12, 2000, which designated the United States of America.

TECHNICAL FIELD

The present invention relates to gradient high performance liquid chromatography using a splitted tubing apparatus in which in order to achieve gradient elution, a mobile phase supplied by a pump is split into plural passages so as to be joined again thereafter.

BACKGROUND ART

A low flow high performance liquid chromatography (HPLC) apparatus using a micro column having an inner diameter of less than 0.1 mm, a semi-micro column or a capillary column is suitable for high-sensitive analysis of trace components, and in particular an HPLC/ESI-MS system connected online to an electro-spray ionization mass spectrometer (ESI-MS) is widely used in various fields. Recently, there have been advances to increase the sensitivity of a spray probe of the ESI-MS, so that an example is reported, in which the measurement at flow velocity from several tens of nano-liters/minute to 1 $\mu$L/min becomes practical (M. Wilm, M. Mann, Anal. Chem., 68 (1996) 1.). Following this, trends toward micronization in the HPLC system are also accelerated, so that a low flow high performance liquid chromatographic system corresponding to the most suitable flow velocity of the ESI is under development. However, it is difficult to achieve a high reproducibility at flow speeds of less than several micro-liters/minute in a low high performance liquid chromatography, so that even in an available micro HPLC system with the highest performance, it is reported that the flow velocity at which the high reproducibility of gradient elution can be obtained is 10–20 $\mu$L/min or more (E. C. Huang, J. D. Henion; Anal. Chem., 63 (1991) 732; A. Ducret, N. Bartone, P. A. Haynes, A. Blanchard, R. Aebersold, AnaL. Biochem., 265 (1998) 129.).

Currently, in order to perform gradient elution at a flow velocity of several micro-liters/minute or less, there are roughly two classes of methods known. These are a pre-column-flow-split method in which the gradient elution is performed at a medium-high flow velocity at which the reproducibility is obtained and the required amount of flow is split therefrom to be used (W. J. Henzel, J. H. Bourell, J. T. Stults, AnaL. Biochem., 187 (1990) 228.; E. C. Huang, J. D. Henion, Anal. Chem., 63 (1991) 732; J. P. Chervet, M. Ursem, J. P. Salzmann, Anal. Chem., 68 (1996) 1507.), and a one-chamber gradient method using one pump and one solvent mixing device (T. Takeuchi, D. Ishii, J. Chromatogr., 253 (1982) 41; J. E. Macnair, G. J. Opiteck, J. W. Jorgenson, M. A. Moseley III, Rapid Commun. Mass Spec. 11 (1997) 1279; A. Ducret, N. Bartone, P. A. Haynes, A. Blanchard, R. Aebersold, Anal. Biochem., 265 (1998) 129)

There are, however, major defects in both the methods. That is, in the pre-column-flow-split method, because a split ratio changes depending on the viscosity of effluent, the precise adjustment of the gradient flow is difficult; the one-chamber gradient method is limited basically to a gradient with an exponentially functional curve, although the instrument thereof is extremely simple and the reproducibility is high.

In a gradient high performance liquid chromatography, in order to analyze and evaluate ultra-micro-organic-components or ultra-micro-impurities in environmental samples or in medicines and the like, there is an extreme demand for the development of an apparatus in which an arbitrary gradient pattern having excellent reproducibility can be readily achieved.

DISCLOSURE OF THE INVENTION

In view of the situations described above, after the eager investigation, the inventors found the following structures to be able to achieve an expected object so as to complete the present invention.

The present invention provides a splitted tubing apparatus which comprises a solvent inlet part, a splitted tubing part splitted into plural two or more tubes, and a solvent outlet part for a gradient high performance chromatography. The present invention also provides gradient high performance chromatography including a splitted tubing apparatus comprising a solvent inlet part, a splitted tubing part splitted into plural two or more tubes; and a solvent outlet part.

Figure 1:
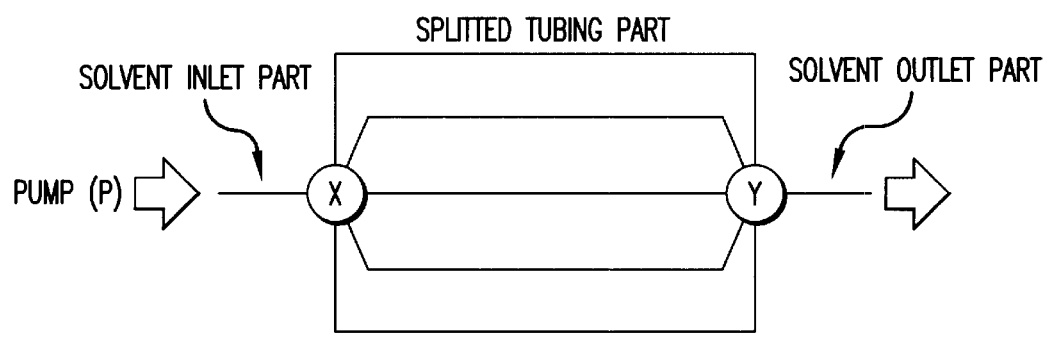
FIG. 1 is a schematic view of a splitted tubing apparatus which comprises a solvent inlet part, a splitted tubing part splitted into plural two or more tubes, and a solvent outlet part, wherein a tube of a solvent inlet part and tubes of a splitted tubing part splitted into plural two or more tubes are connected together via a connector (X), and the tubes of the splitted tubing part and a tube of a solvent outlet part are connected together via a connector (Y).

The present invention also provides a splitted tubing apparatus for a gradient high performance chromatography, in which, as shown in FIG. 1, a tube of a solvent inlet part and tubes of a splitted tubing part splitted into plural two or more tubes are connected together via a connector (X), and the tubes of the splitted tubing part and a tube of a solvent outlet part are connected together via a connector (Y). That is, a mobile phase supplied by a pump (P) is splitted into plural passages at the connector (X) so as to join again thereafter at the connector (Y).

The present invention also provides an analyzing method of trace components in a sample, in which after a mobile phase is fed to the splitted tubing apparatus by a pump (P) so as to sequentially fill the solvent inlet part, the splitted tubing part splitted into plural two or more tubes, and the solvent outlet part, a target component is eluted from a separation column according to an arbitrary gradient-elution linear line or curve by feeding a mobile phase with a different composition.

The splitted tubing apparatus is used by connecting to the pump (P) via a tube. The splitted tubing part of the splitted tubing apparatus between the solvent inlet part and the solvent outlet part is formed of plural tubes, which are the same or different in length and/or inner diameter, arranged in parallel, enabling an arbitrary gradient-elution pattern to be readily performed. In the splitted tubing part of the splitted tubing apparatus: for example, plural tubes having the same inner diameter and only different lengths may be arranged in parallel; plural tubes having the same length and only different inner diameters may be arranged in parallel; or plural tubes having different both inner diameters and lengths may be arranged in parallel.

Also, each inner diameter of splitted tubes arranged in parallel may vary at an intermediate portion of the tube; or a new connector may be arranged at an intermediate portion of each splitted tube so that tubes across the connector may have different inner diameters so as to be connected together.

The lengths of plural splitted tubes of the splitted tubing apparatus between the solvent inlet part and the solvent outlet part are not limited, and the inner diameters of the tubes may be changed from several micro-meters to 1 mm or from 1 $\mu$m to 1 mm. Each material of the splitted tubes and the connectors may be stainless steel, glass, or a synthetic resin, for example; however, it is not specifically limited. In addition, as the synthetic resin, there may be polyether ether ketone (PEEK) and Teflon, for example.

In the splitted tubing part of the splitted tubing apparatus between the solvent inlet part and the solvent outlet part, the number of the plural splitted tubes, i.e., the number of splits at the passage of the connector (X) shown in FIG. 1, may be not limited as long as it is 2 or more; with increasing the number of more than three splits, a finer gradient elution pattern can be readily established.

By allowing to pass through the splitted tubing apparatus, the mobile phase has a step-gradient mobile-phase system when passing through the solvent outlet part of the splitted tubing apparatus.

The present invention also provides a splitted tubing apparatus for a gradient high performance liquid chromatography, in which a mobile phase eluted from the tube of the solvent outlet part of the splitted tubing apparatus is allowed to flow into the solvent mixing device.

That is, the solvent mixing device is connected to the splitted tubing apparatus shown in FIG. 1, so that a mobile phase supplied from the pump (P) is allowed to sequentially pass through the splitted tubing apparatus and the solvent mixing device in that order. By allowing to pass through the splitted tubing apparatus, a mobile phase having a step-gradient mobile-phase composition can be obtained; thereafter, by allowing to pass through the solvent mixing device, by which alone, a gradient composition with an exponentially functional curve could be obtained, a linear line gradient (linear gradient) or linear-gradient like arbitrary gradient elution pattern can be obtained by superimposing both the different gradient compositions.

As the solvent mixing device, there may be a chamber device in which agitation and mixing are performed with an agitator and the like or an available mixing connector device; however, it is not of course limited to those and a device of any structure may be used as long as it can efficiently mix the mobile phase solvents fed thereto.

Furthermore, in the splitted tubing apparatus, in which a mobile phase supplied from the pump (P) is splitted into plural passages at the connector (X) so as to join again at the connector (Y), as shown in FIG. 1, the present invention provides a splitted tubing apparatus for a gradient high-performance liquid chromatography, in which the connector (Y) has a function for mixing solvents. That is, in the splitted tubing apparatus with the connector (Y) having a function for mixing solvents, by allowing a mobile phase supplied from the pump (P) to pass through the splitted tubing apparatus, a linear gradient or linear-gradient like arbitrary gradient elution pattern can be obtained. Accordingly, in the splitted tubing apparatus with the connector (Y) having a function for mixing solvents, in order to achieve a linear gradient or linear-gradient like arbitrary gradient elution pattern, the solvent outlet part of the splitted tubing apparatus need not to be connected to a different solvent mixing device.

As a solvent mixing device, a mixing connector device and/or a connector (Y) having a function for mixing solvents to which splitted tubes in the splitted tubing apparatus are joined are required to have a sufficient mixing function of mobile phases. As the structures for this purpose, there may be: 1) a mixer capacity inside the connector (dead volume) is increased sufficient enough relative to the velocity of the mobile phase; 2) a mixer inside the connector is made to have a shape suitable for mixing the solvent-flow; and 3) a frit (film) is formed, for example. However, they are not limited to these. In addition, it is preferable that the mixer internal capacity (dead volume) of the solvent mixing device or the connector (Y) having a function for mixing solvents in the splitted tubing be from 2 to 1000 relative to 1 for the velocity of the mobile phase (the moving volume per minute of the mobile phase).

As the frit (film) in the solvent mixing device or the connector (Y), there may be a sintered filter, ceramics, metallic mesh, or cellulose fiber, for example; however, it is of course not limited to these.

The splitted tubing apparatus for a gradient high performance liquid chromatography according to the present invention can be widely used for from a normal gradient high performance liquid chromatography used at a flow rate of several milli-liters per minute, i.e., from 0.1 to 3 ml/m, for example, to a low flow gradient high performance liquid chromatography used at an extremely low speed. In particular, when using for the low flow gradient high performance liquid chromatography, the usefulness of the splitted tubing apparatus according to the present invention is much more displayed; however, it is of course not limited to this.

As the low flow gradient high performance liquid chromatography, there may be: a gradient micro high performance liquid chromatography having a micro-column with an inner diameter of 0.5 to 1 mm and used at a flow rate of several tens micro-litters per minute, i.e., from 10 to 90 $\mu L/m$, for example; a gradient semi-micro high performance liquid chromatography having a semi-micro-column with an inner diameter of 1 to 2.5 mm and used at a flow rate of 50 to 250 $\mu L/m$; or a gradient capillary high performance liquid chromatography having a capillary column with an inner diameter of less than 0.5 mm and used at a flow rate of less than several micro-litters per minute, i.e., less than 10 $\mu L/m$ normally.

An example of the low flow gradient high performance liquid chromatography in which the splitted tubing apparatus according to the present invention is arranged will be described below in detail; however, the present invention is not limited to these.

Figure 2:
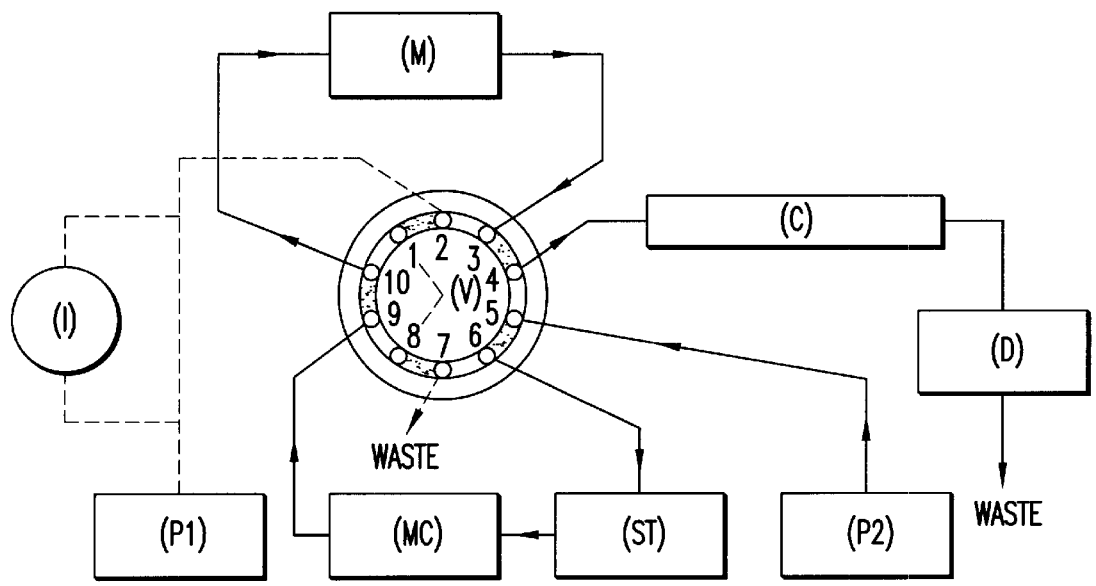
FIG. 2 is a schematic view of a gradient high performance liquid chromatographic system having the splitted tubing apparatus (ST) and a solvent mixing device (MC) connected to the splitted tubing apparatus arranged therein.

The present invention provides a low flow gradient high performance chromatography in which a pump (P1), an injector (I), a switching valve (V), a column for concentrating components (M), the switching valve (V), a solvent mixing device (MC), a splitted tubing apparatus (ST), and the switching valve (V) are connected in that order, and along another line, a pump (P2), the switching valve (V), the splitted tubing apparatus (ST), the solvent mixing device (MC), the switching valve (V), the column for concentrating components (M), the switching valve (V), a separating column (C), and a detector (D) are connected in that order, as shown in FIG. 2.

The present invention also provides an analyzing method of trace components in a sample in that in the above described low flow gradient high performance liquid chromatography, from a mobile phase supplied by the pump (P1), a target component is acquired in the column for concentrating components (M); then, by switching the switching valve (V), the mobile phase is fed to the splitted tubing apparatus (ST) and the solvent mixing device (MC) in that order by the pump (P2), so that a mobile phase with a linear gradient or linear-gradient like arbitrary composition is formulated so as to allow the target component to be gradient-eluted from the separating column (C).

Figure 3:
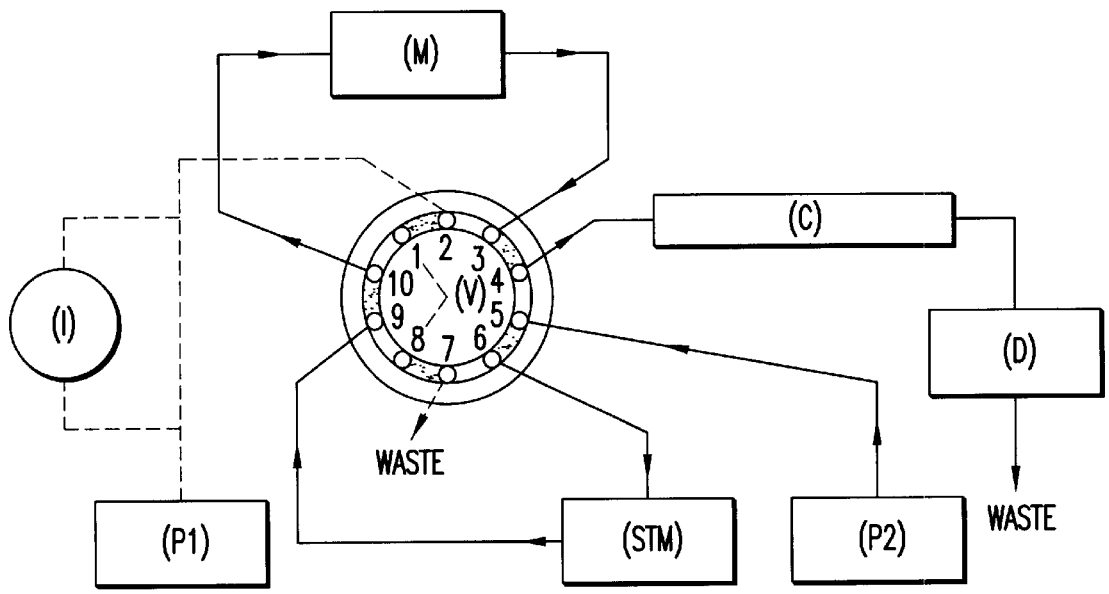
FIG. 3 is a schematic view of a gradient high performance liquid chromatographic system having a splitted tubing apparatus having a function for mixing solvents (STM) arranged therein.

Furthermore, the present invention provides a low flow gradient high performance liquid chromatography in which a pump (P1), an injector (I), a switching valve (V), a column for concentrating components (M), the switching valve (V), a splitted tubing apparatus having a function for mixing solvents (STM), and the switching valve (V) are connected together in that order, and along another line, a pump (P2), the switching valve (V), the splitted tubing apparatus having a function for mixing solvents (STM), the switching valve (V), the column for concentrating components (M), the switching valve (V), a separating column (C), and a detector (D) are connected together in that order, as shown in FIG. 3.

The present invention also provides an analyzing method of trace components in samples in that in the above described low flow gradient high performance liquid chromatography, from a mobile phase supplied by the pump (P1), a target component is acquired in the column for concentrating components (M); then, by switching the switching valve (V), the mobile phase is fed to the splitted tubing apparatus having a function for mixing solvents (STM) by a pump (P2), so that a mobile phase with a linear gradient or linear-gradient like arbitrary composition is formed so as to allow the target component to be gradient-eluted from the separating column (C).

Arranging a splitted tubing apparatus according to the present invention in a gradient high performance liquid chromatography formed as follows results in a system capable of analyzing trace components at a high-speed and high-sensitivity according to an arbitrary gradient straight line or curve.

FIG. 1 shows a splitted tubing apparatus according to the present invention; FIGS. 2 and 3 are schematic representations of samples of a low flow gradient high performance liquid chromatography including the splitted tubing apparatus; the present invention is not certainly limited to these. The system will be described in detail with reference to FIGS. 1 to 3.

FIG. 1 is a drawing of a splitted tubing apparatus for a gradient high performance liquid chromatography according to the present invention, which comprises a tube of a solvent inlet part at one of both ends and a tube of a solvent outlet part at the other end, wherein the tube between the tube of the solvent inlet part and the tube of the solvent outlet part is splitted into two or more plural tubes. A mobile phase supplied by a liquid (P) enters into the apparatus from a solvent inlet part at one end so as to join again at a connector (Y) after being divided into plural tubes at a connector (X), so that the mobile phase flows out of the tube of the solvent outlet part at the other end. In the splitted tubing apparatus, after a mobile phase is fed to the splitted tubing apparatus by the pump (P) so as to sequentially fill the solvent inlet part, the splitted tubing part splitted into plural two or more tubes, and the solvent outlet part, a mobile phase with another composition is fed so that a target component can be eluted according to an arbitrary gradient elution straight line or curve from a separating column.

The flow velocity in the solvent inlet part is divided after a mobile phase passes through the connector (X) according to the resistance of each of splitted tubes, so that the mobile phase in each of plural splitted tubes connected to the connector (X) moves at a different flow-velocity in the splitted tube. Because the resistance of each of plural splitted tubes depends on the length and/or inner diameter of the tube, the flow velocity in each of the splitted tubes can be changed by changing the length and/or inner diameter of the splitted tube so as to produce shifts in time at which the mobile phase approaches the connector (Y) to join. An apparatus creating an arbitrary gradient pattern by utilizing the shift in time for approaching the connector (Y) via each splitted tube is a splitted tubing apparatus according to the present invention.

In a gradient high performance liquid chromatography, especially in a low flow gradient high performance liquid chromatography, when step-gradient eluting, the splitted tubing apparatus shown in FIG. 1 is used by connecting the tube of the solvent inlet to the pump and the tube of the solvent outlet to the separating column. Also, during linear gradient or linear-gradient like arbitrary eluting, the splitted tubing apparatus shown in FIG. 1 is used by connecting the tube of the solvent inlet to the pump and the tube of the solvent outlet is connected to the separating column after connecting to the solvent mixing device. However, when the connector (Y), to which plural splitted tubes in the splitted tubing apparatus shown in FIG. 1 are joined, has a function for mixing solvents, the splitted tubing apparatus is not required to connect to the solvent mixing device, wherein by connecting the tube of the solvent inlet in the splitted tubing apparatus shown in FIG. 1 to the pump and the tube of the solvent outlet to the separating column, a mobile phase with a linear gradient or linear-gradient like arbitrary composition can be formed.

Arranging a splitted tubing apparatus according to the present invention in a low flow gradient high performance liquid chromatography formed as follows results in forming a mobile phase with a linear gradient or linear gradient-like arbitrary composition. Therefore, the system becomes to be suitable for an analysis of trace components at high speed and high sensitivity.

FIG. 2 is a schematic view of a low flow gradient high performance liquid chromatography, in which a pump (P1), an injector (I), a switching valve (V), a column for concentrating components (M), the switching valve (V), a solvent mixing device (MC), a splitted tubing apparatus (ST), and the switching valve (V) are connected together in that order, and along another line, a pump (P2), the switching valve (V), the splitted tubing apparatus (ST), the solvent mixing device (MC), the switching valve (V), the column for concentrating components (M), the switching valve (V), a separating column (C), and a detector (D) are connected together in that order. A method for concentrating and separating components in the low flow gradient high performance liquid chromatography is described as follows.

(1) A mobile phase for concentrating components is fed from the pump (P1); sample solution is injected from the injector (I); the sample is supplied to the column for concentrating components (M) while diluting the sample solution with the mobile phase for concentrating components, so that a target component in the sample is captured in the column for concentrating components (M). Simultaneously, the solvent mixing device (MC) and the splitted tubing apparatus (ST) are filled with the mobile phase for concentrating components. The mobile phase for concentrating components means a mobile phase for allowing the target component to be absorbed in the column for concentrating components, and the mobile phase is a solvent with a comparatively large polarity such as water when the column for concentrating components has a hydrophobic property.

(2) Next, by switching the valve (V), a mobile phase for separating samples fed from the pump (P2) is discharged via the splitted tubing apparatus (ST), the solvent mixing device (MC), the column for concentrating components (M), the separating column (C), and the detector (D). The mobile phase for separating samples means a mobile phase for allowing a sample component to be released from the column for concentrating components (M) and furthermore for separating the sample component in the separating column (C), and the mobile phase for separating samples is a solvent with a polarity smaller than that of the mobile phase for concentrating components, such as methanol and acetonitrile, when the column for concentrating components (M) has a hydrophobic property. At this time, the mobile phase for concentrating components is mixed with the mobile phase for separating samples in the splitted tubing apparatus (ST) and the solvent mixing device (MC), and is fed to the column for concentrating components (M) while forming a gradient in the mixture of the both mobile phases so as to allow the captured target component in the sample to be released, so that a sample band including the target component is introduced in the separation column. When the mobile phase for concentrating components and the mobile phase for separating samples pass through the splitted tubing apparatus (ST), a step gradient is formed in the mixture of the both mobile phases, and furthermore, when passing through the solvent mixing device (MC) connected to the splitted tubing apparatus (ST), a mobile phase with a linear gradient or linear-like arbitrary composition is formed.

Accordingly, in the low flow gradient high performance liquid chromatography, the separation and analysis of the trace target component with high sensitivity can be achieved; this is one of the features of the present invention. Also, this system can be combined with various functional films as the column for concentrating components (M) in order to concentrate the target component, so that the wide applicability is also one of the features.

As the pump, there may be a syringe pump and a pump with a plunger, for example; it may be preferably a pump for low flow gradient high performance liquid chromatography. As the valve, there may be a ten-way and a six-way valve for a high performance liquid chromatography. The injector is a device for injecting sample solution into the high performance liquid chromatography; the separating column is a column for separating the target component in the sample, in which a so-called normal-phase column, a reversed-phase column, and so forth may be selected according to the object. As these devices, commercially available products may be used.

Another system of a low flow gradient high performance liquid chromatography according to the present invention will be described with reference to FIG. 3. FIG. 3 is a schematic view of a low flow gradient high performance liquid chromatography, in which the pump (P1), the injector (I), the switching valve (V), the column for concentrating components (M), the switching valve (V), the splitted tubing apparatus having a function for mixing solvents (STM), and the switching valve (V) are connected together in that order, and along another line, the pump (P2), the switching valve (V), the splitted tubing apparatus having a function for mixing solvents (STM), the switching valve (V), the column for concentrating components (M), the switching valve (V), the separating column (C), and the detector (D) are connected together in that order.

A method for concentrating and separating components in the system shown in FIG. 3 is described as follows.

(1) A mobile phase for concentrating components is fed from the pump (P1); sample solution is injected from the injector (I); the sample is supplied to the column for concentrating components (M) while diluting the sample solution with the mobile phase for concentrating components, so that a target component in the sample is captured in the column for concentrating components (M). Simultaneously, the splitted tubing apparatus having a function for mixing solvents (STM) is filled with the mobile phase for concentrating components.

(2) Next, by switching the valve (V), a mobile phase for separating samples fed from the pump (P2) is discharged via the splitted tubing apparatus having a function for mixing solvents (STM), the column for concentrating components (M), the separating column (C), and the detector (D). At this time, the mobile phase for concentrating components is mixed with the mobile phase for separating samples in the splitted tubing apparatus having a function for mixing solvents (STM), and is fed to the column for concentrating components (M) while forming a gradient in the mixture of the both mobile phases so as to allow the captured target component in the sample to be released, so that a sample band including the target component is introduced in the separation column. When the mobile phase for concentrating components and the mobile phase for separating samples pass through the splitted tubing apparatus having a function for mixing solvents (STM), a mobile phase with a linear gradient or linear-like gradient arbitrary composition is formed. At this time, the flow direction of the mobile phase for separating samples passing through the splitted tubing apparatus having a function for mixing solvents (STM) is opposite to that of the sample solution being injected.

According to the present invention, in a gradient high performance liquid chromatography, especially in a low flow gradient high performance liquid chromatography, by arranging the splitted tubing apparatus (ST) and the solvent mixing device (MC) to be connected to each other or by arranging the splitted tubing apparatus having a function for mixing solvents (STM), an arbitrary gradient-elution straight line or curve can be freely designed, enabling an arbitrary gradient-elution system to be controlled with high-reproducibility on a nano-scale. Accordingly, a target trace component can be separated and analyzed with high sensitivity according to the present invention.

EXPERIMENTAL EXAMPLES

Figure 6:
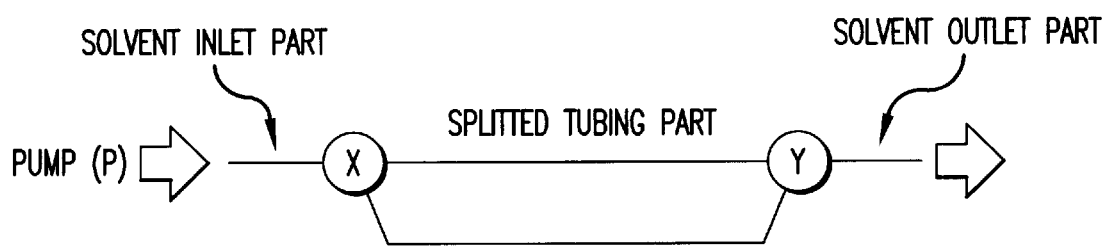
FIG. 6 is a schematic view of a splitted tubing apparatus in which a splitted tubing part arranged between a solvent inlet part and a solvent outlet part has two splitted tubes with different lengths.

1) The effect of the splitted tubing apparatus on a gradient pattern in the gradient high performance liquid chromatography As shown in FIG. 6, between tubes of the solvent inlet part and the solvent outlet part, i.e., between the connector (X) and the connector (Y), by using a splitted tubing apparatus in which two tubes with the same inner diameter (100 $\mu$m) and different lengths (10 cm and 20 cm) are splitted, a system was established such that a pump, the splitted tubing apparatus shown in FIG. 6, and a UV detector were connected together in that order with tubes for HPLC with an inner diameter of 50 $\mu$m. In this system, the effect in the inside of the splitted tubing apparatus on a gradient pattern was investigated by the following methods.

Figure 7:
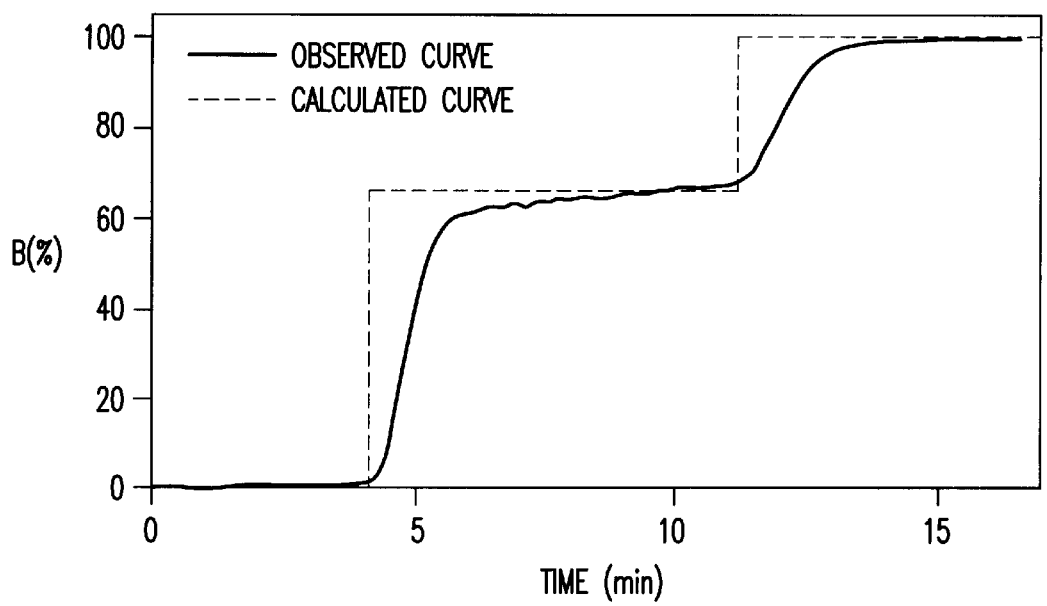
FIG. 7 is a gradient elution curve (a curve of changes with time in B-liquid consistency of a mobile phase component) in a low flow gradient high performance chromatography having a splitted tubing apparatus arranged therein.

That is, distilled water for HPLC as an A liquid was fed at a flow velocity of 0.5 ml/min so as to measure a liquid weight flowing into the connector (Y) per unit time from each of the splitted tubes, and the flow ratio (split ratio) divided into each splitted tube from the connector (X) was calculated on the basis of the weight ratio. Also, after the entire system was filled with the A liquid fed from the pump, the pump was temporarily stopped and it was replaced with a syringe (Hamillton #1702 for 25 ml) containing 10% methanol water solution including 0.1% formamide (a B liquid); then, liquid supply was started at a flow rate of 0.5 ml/min so as to evaluate changes in the absorbance at a wavelength of 210 nm with a lapse of time. From the result of the changes with time in the absorbance of the B liquid, changes with time of the B liquid consistency in the mobile phase composition are shown in FIG. 7. Also, the result of the simulation based on the calculation is simultaneously shown in FIG. 7. In addition, as the pump, a syringe pump of Harvard Model 22, as the detector, a JASCO 870-CE UV detector, as an analyzer, a Shimazu C-R4A integrator, as the connector (X), a JOUR peak tee connector (Shimazu), and as the connector (Y), a JOUR peak mixing tee connector (Shimazu) was used, respectively.

The split ratio into each splitted tube in the connector (X) was approximately 2:1=the flow velocity in a 10 cm tube: the flow velocity in a 20 cm tube. Therefore, it is apparent that the split ratio of the mobile phase can be controlled by the length ratio of plural splitted tubes in the splitted tubing apparatus.

Also, as shown in FIG. 7, the B liquid consistency in the mobile phase was changed in a step gradient pattern according to the system. Moreover, the step gradient pattern substantially agrees with calculated values based on a simulation formula shown below, although being somewhat smoothed in comparison with the calculated values. Accordingly, it is apparent to be able to control an arbitrary step-gradient change in a mobile phase composition by using the splitted tubing apparatus.

Equations for Simulation $$B(t) = 0 \quad (0 \leq t \leq ta) \tag{1}$$

$$0 \leq B(t) \leq Fb/F \times 100 \quad (t = ta) \tag{2}$$

$$B(t) = Fb/F \times 100 \quad (ta \leq t \leq tb) \tag{3}$$

$$Fb/F \times 100 \leq B(t) \leq 100 \quad (t = tb) \tag{4}$$

$$B(t) = 100 \quad (tb \leq t) \tag{5}$$

Wherein $$ta = Va/Fa + tD \tag{6}$$

$$tb = Vb/Fb + tD \tag{7}$$

B(t): B liquid consistency (%) in a mobile phase at time t (min)

tD: time of the B liquid to reach the connector (X) from the pump (delay time) (min)

F: flow rate (mL/min)

Fa: flow rate in the 10 cm tube (shorter tube) (mL/min)

Fb: flow rate in the 20 cm tube (longer tube) (mL/min)

Va: volume of the 10 cm tube (shorter tube) (mL)

Vb: volume of the 20 cm tube (longer tube) (mL)

2) The effect of the splitted tubing apparatus having a function for mixing solvents on a gradient pattern in the gradient high performance liquid chromatography having the splitted tubing apparatus having a function for mixing solvents arranged therein.

Figure 5:
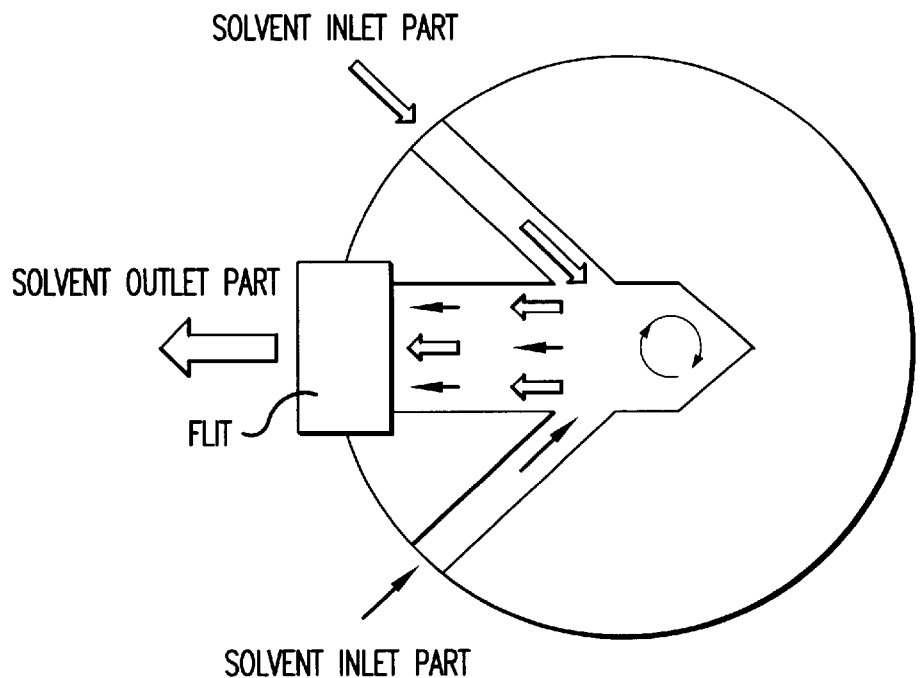
FIG. 5 shows an internal structure of a peak-mixing tee (Shimazu) having a function for mixing solvents.

In the splitted tubing apparatus shown in FIG. 6, as the connector (Y) to which two splitted tubes join, a peak mixing tee having a function for mixing solvents (Shimazu) shown in FIG. 5 was used. That is, the connector (Y) having a mixing function has a mixing capacity of several milliliters inside into which mobile phases flow through two tubes from the solvent inlet part so as to be mixed with solvent flow. Furthermore, allowing the mixture to pass through a frit arranged before the solvent outlet part enables the solvents to be sufficiently mixed, enabling the mobile phase solvents to be mixed with high mixing-efficiency and reproducibility. By using the low flow gradient high performance liquid chromatography having the splitted tubing apparatus having a function for mixing solvents (STM) arranged therein, the effect of the splitted tubing apparatus having a function for mixing solvents on a gradient pattern was investigated following a method below.

The tubes of the solvent inlet part and the solvent outlet part, i.e., the connector (X) and the connector (Y) were connected together with divided two tubes having the same inner diameter (100 $\mu$m) and different lengths (10 cm and 20 cm), as shown in FIG. 6. Moreover, the connector (Y) shown in FIG. 5 was used for the splitted tubing apparatus having a function for mixing solvents, and the pump, the splitted tubing apparatus having a function for mixing solvents, a UV detector were connected together in that order with tubes for HPLC having an inner diameter of 50 μm. Distilled water for HPLC as A liquid was fed from the pump at a flow rate of 0.5 mL/min so as to fill the entire system with the A liquid supplied from the pump; then, the pump was temporarily stopped and replaced with a syringe (Hamilton #1702 for 25 mL) containing 10% methanol water solution including 0.1% formamide (B liquid); then, the liquid was started to supply at a flow rate of 0.5 mL/min, and changes with a laps of time in the absorbance at a wavelength of 210 nm were evaluated.

Figure 8:
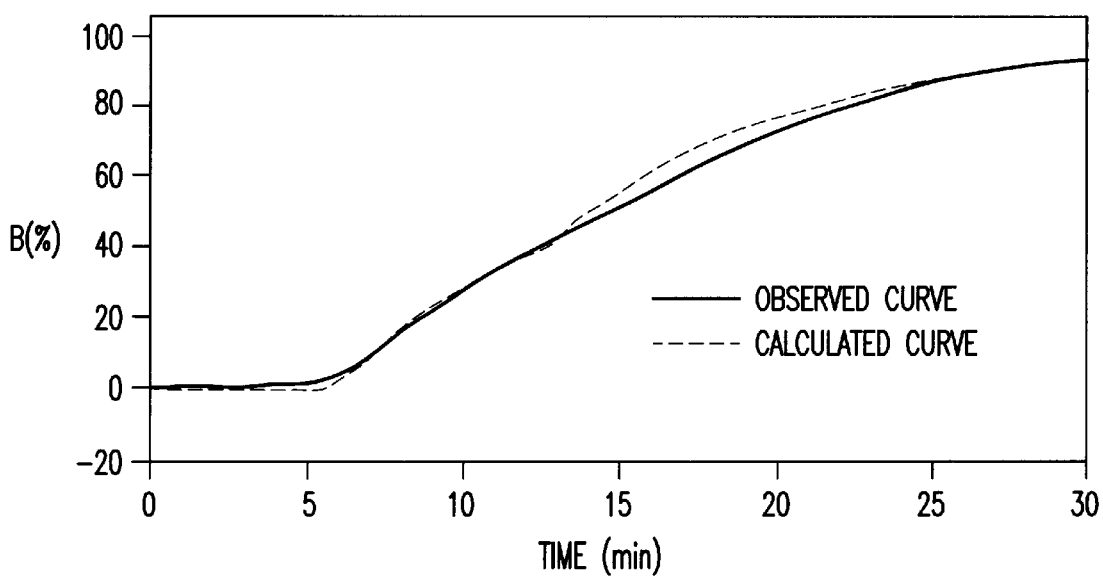
FIG. 8 is a gradient elution curve (a curve of changes with time in B-liquid consistency of a mobile phase component) in a low flow gradient high performance chromatography in which a splitted tubing apparatus having a function for mixing solvents is provided.

FIG. 8 shows changes with time in the B liquid consistency in the mobile phase obtained from the result of changes with time in the absorbance after supplying the B liquid and the result of calculated simulation.

As shown in FIG. 8, according to this system, the B liquid consistency in the mobile phase is changed in a linear line gradient (linear gradient) or linear gradient-like pattern. Moreover, the linear gradient or linear gradient-like arbitrary gradient elution pattern quite agrees with the simulation curve based on the simulation formula, so that it is apparent that the elution curve can be controlled by the combination of both the step gradient caused by the splitted tubing apparatus and the one-chamber gradient (a gradient of an exponential function) produced by the connector (Y) in the splitted tubing apparatus having a function for mixing solvents. That is, in the low flow gradient high performance liquid chromatography, by using the splitted tubing apparatus having a function for mixing solvents (STM), it is apparent that a linear gradient or linear gradient-like arbitrary gradient change in the mobile phase composition can be controlled.

Equations for Simulation

The simulation curve was calculated from the theoretical equations on the step gradient produced by the splitted tubing apparatus (the proceeding equations (1) to (7)) and on the one-chamber gradient method produced by the solvent mixing device (T. Tackeuchi, D. Ishii, J. Chromatogr., 253 (1982) 41; J. E. Macnair, G. J. Opiteck, J. W. Jorgenson, M. A. Moseley III, Rapid Commun. Mass Spec. 11 (1997) 1279; A. Ducret, N. Bartone, P. A. Haynes, A. Blanchard, R. Aeyersold, AnaL. Biochem., 265 (1998) 129). In addition, the theoretical equations on the one-chamber gradient method are as follows:

$$B(t)=0 \ (0 \leq t \leq tD) \quad (8)$$

$$B(t)=(1-e^{-F(t-tD)/Vx}) \times 100 \ (t \geq tD) \quad (9)$$

F: flow rate (mL/min)

Vx: volume of the mixer (mL)

From the equations (1) to (9), the simulation when using the splitted tubing apparatus having the mixing device arranged therein or the splitted tubing apparatus having the connector (Y) having a function for sufficiently mixing solvents to which plural splitted tubes join was calculated from the equations below.

$$B(t)=0 \ (0 \leq t \leq ta) \quad (10)$$

$$B(t)=(1-e^{-F(t-tD)/Vx}) \times 100 \times Fa/F \ (ta \leq t \leq tb) \quad (11)$$

$$B(t)=(1-e^{-F(t-tD)/Vx}) \times (100-B(tb)) \ (tb \leq t) \quad (12)$$

3) The effect of the splitted tubing apparatus having the solvent mixing device connected thereto on a gradient pattern in the low flow gradient high performance liquid chromatography.

In the low flow gradient high performance liquid chromatography shown in FIG. 2, by assembling the splitted tubing apparatus (ST) shown in FIG. 4 thereinto, the gradient-elution was performed by the method below so as to investigate the effect of the splitted tubing apparatus (ST) having the solvent mixing device (a chamber capacity of 120 mL) connected thereto on a gradient elution pattern. However, the gradient elution was evaluated in a state that the column for concentrating components (M) and the separating column (C) were not arranged to the low flow gradient high performance liquid chromatography in that order to enable to evaluate the effect of the splitted tubing apparatus easily.

Figure 4:
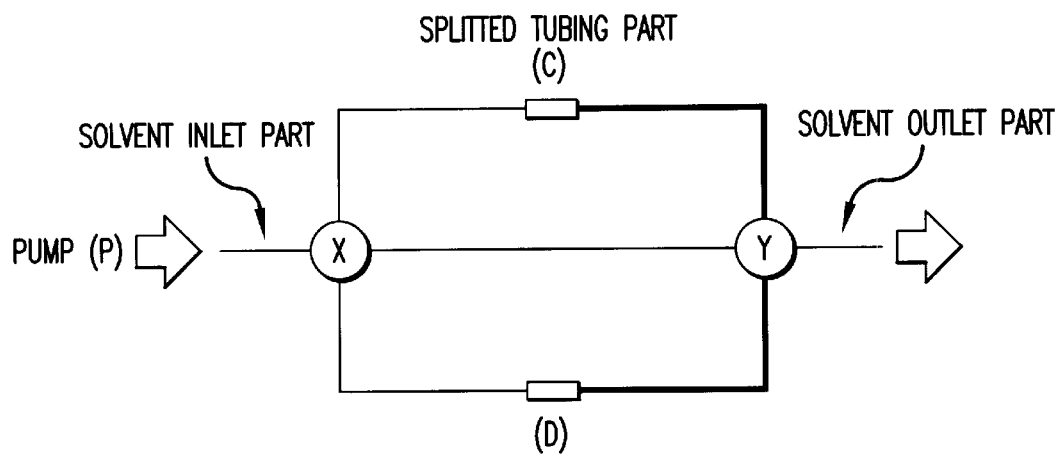
FIG. 4 is a schematic view of a splitted tubing apparatus which comprises a solvent inlet part, a splitted tubing part splitted into three tubes, and a solvent outlet part, wherein connectors (C) and (D) are further arranged in intermediate portions of the splitted tubes so that the respective tubes across the connectors (C) and (D) with different diameters are connected to each other.
Figure 9:
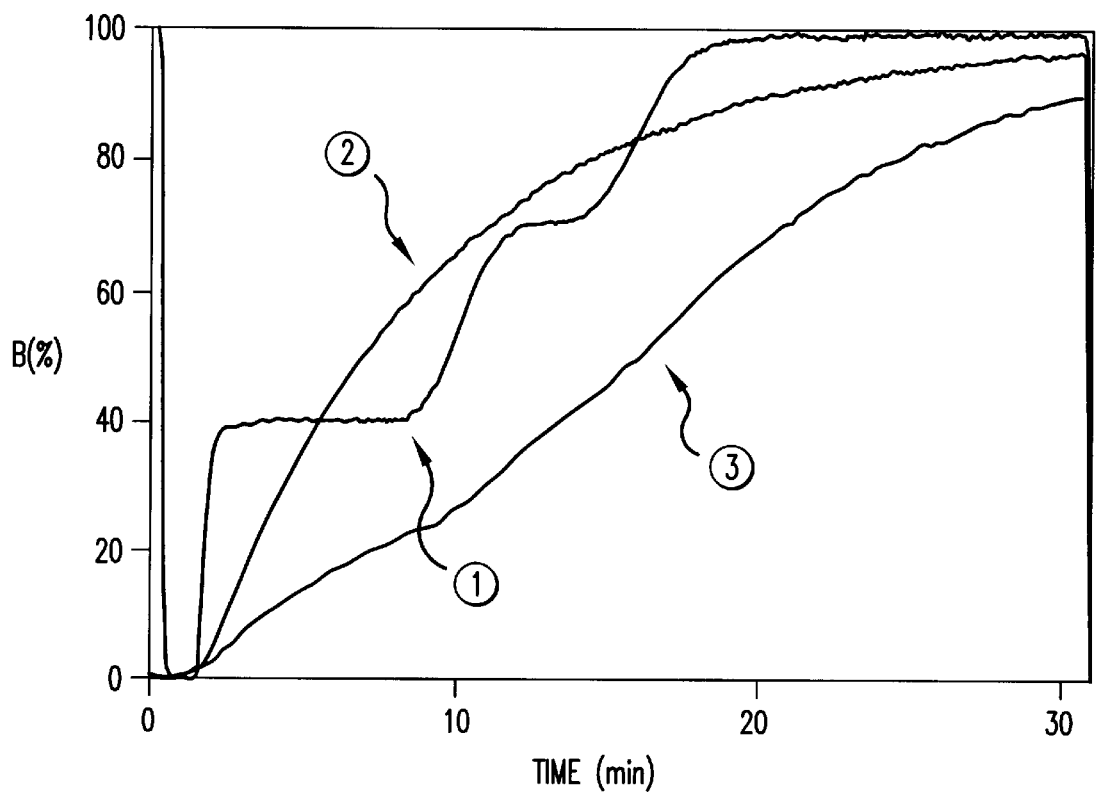
FIG. 9 is a gradient elution curve (a curve of changes with time in B-liquid consistency of a mobile phase component) in a low flow gradient high performance chromatography having 3) a splitted tubing apparatus (ST) arranged therein and having a solvent mixing device (MC) connected to the splitted tubing apparatus. For comparison, there are gradient elution curves (curves of changes with time in B-liquid consistency of a mobile phase component) in low-speed gradient high-performance chromatography for the case 1) of not having a solvent mixing device (MC) attached thereto (having the splitted tubing apparatus (ST) attached thereto), and for the case 2) of not having the splitted tubing apparatus (ST) (having the solvent mixing device (MC) attached thereto).

In addition, in the splitted tubing apparatus shown in FIG. 4, 4-way connectors were used as the connectors (X) and (Y), and the apparatus was constructed such that the mobile phase fed from the pump (P) was divided into three passages at the connector (X) so as to be joined again at the connector (Y). Furthermore, in the apparatus, connectors (C) and (D) arranged in intermediate portions of splitted tubes, so that tubes with different inner diameters were connected together across the respective connectors (C) and (D). The inner diameter and length of the respective splitted tubes in the splitted tubing apparatus (ST) shown in FIG. 4 are as follows:

The tube connecting between the connector (X) and the connector (C): 0.1 mm inner diameter×100 mm length The tube connecting between the connector (X) and the connector (Y): 0.1 mm inner diameter×100 mm length The tube connecting between the connector (X) and the connector (D): 0.1 mm inner diameter×100 mm length The tube connecting between the connector (Y) and the connector (C): 0.8 mm inner diameter×50 mm length The tube connecting between the connector (Y) and the connector (D): 0.8 mm inner diameter×100 mm length First, distilled water for HPLC was fed as A liquid at a flow rate of 20 mL/min by the pump (P1) so as to fill the entire system with the distilled water for HPLC in a sequence of the injector (I), the switching valve (V), the solvent mixing device (MC), and the splitted tubing apparatus (ST). shown in FIG. 4. Next, by switching the valve (V), 0.3% acetone water solution was fed as B liquid at a flow rate of 20 mL/min by the pump (P2) so as to allow to flow through the splitted tubing apparatus (ST) shown in FIG. 4 and the solvent mixing device (MC) in that order, so that changes in the absorbance with a lapse of time at a wavelength of 254 nm were evaluated by the detector (D). FIG. 9 shows changes in the B liquid consistency obtained from the result. of the changes in the absorbance with time after feeding the B liquid. In addition, for comparison, in the low flow gradient high performance chromatography shown in FIG. 2, the evaluations, were also performed in the case 1) of not having the solvent mixing device (MC) attached thereto (having the splitted tubing apparatus (ST) attached thereto), and in the case 2) of not having the splitted tubing apparatus (ST) (having the solvent mixing device (MC) attached thereto).

When 0.3% acetone water solution was fed as B liquid at a flow rate of 20 mL/min by the pump (P2), the liquid weight per unit time of the liquid flowing into the connector (Y) of the splitted tubing apparatus shown in FIG. 4 from each splitted tube was also measured and the flow ratio of the three splitted tubes (split ratio) was calculated on the basis of the weight ratio.

In the splitted tubing apparatus shown in FIG. 4, the initial flow-rate in the solvent inlet part was divided into each mobile phase flow-rate in each tube splitted into three tubes at the connector (X) substantially at a ratio of 1:1:1 after the mobile phase passed through the connector (X). Therefore, it is apparent that the split ratio can be controlled by the ratio of the plural splitted tubes in the splitted tubing apparatus in the length and/or inner diameter.

Also, in the low flow gradient high performance liquid chromatography shown in FIG. 2, as shown in FIG. 9, in the case 1) of not having a solvent mixing device (MC) attached thereto (having the splitted tubing apparatus (ST) attached thereto), the chromatography became step gradient; in the case 2) of not having the splitted tubing apparatus (ST) (having the solvent mixing device (MC) attached thereto), it became one-chamber gradient, i.e., exponentially gradient. In contrast, when the splitted tubing apparatus (ST) and the solvent mixing device (MC) were connected together, a linear gradient or a linear-gradient like gradient was obtained.

From the results above, in the low flow gradient high performance liquid chromatography, it is apparent that by connecting the solvent mixing device (MC) to the splitted tubing apparatus (ST), changes in the linear gradient or linear-gradient like arbitrary gradient of the mobile phase composition can be controlled.

What is claimed is:

1. A method of analyzing trace components in a sample, which comprises the steps of:
    feeding a mobile phase into a split tubing apparatus by a pump (P); wherein said split tubing apparatus comprises
        a solvent inlet part;
        a split tubing part split into a plurality of two or more tubes;
        a solvent outlet part;
        a connector (X); and
        a connector (Y),
        wherein at least one tube is connected together between the solvent inlet part and the split tubing part split into a plurality of two or more tubes via the connector (X) and wherein the split tubing part split into a plurality of two or more tubes is connected to connector (Y) and wherein at least one tube is connected together between connector (Y) and the solvent outlet part;
    sequentially filling the solvent inlet part, the split tubing part split into a plurality of two or more tubes, and the solvent outlet part with the mobile phase;
    eluting a target component from a separation column according to an arbitrary gradient-elution linear line or curve by feeding a mobile phase with a different composition; and
    flowing a mobile phase discharged from the tube of the solvent outlet part into a solvent mixing device.

2. The method of analyzing trace components in a sample according to claim 1, wherein said split tubing apparatus further comprises a plurality of tubes each having the same or different length and/or internal diameter.

3. A low flow gradient high performance liquid chromatography apparatus comprising:
    a line of components connected so a first mobile phase enters said components in the following order; (1) a pump (P1), 2) an injector (I), 3) a switching valve (V), 4) a column for concentrating components (M), 5) the switching valve (V), 6) a solvent mixing device (MC), 7) a split tubing apparatus (ST) comprising
        a solvent inlet part connected by at least one tube to a split tubing part split into a plurality of two or more tubes, and a solvent outlet part connected by at least one tube to the split tubing part split into a plurality of two or more tubes; and
    8) the switching valve (V): and
    another line of components connected so a second mobile phase enters said components in the following order; 1) a pump (P2), 2) the switching valve (V), 3) said split tubing apparatus (ST), 4) the solvent mixing device (MC), 5) the switching valve (V), 6) the column for concentrating components (M), 7) the switching valve (V), 8) a separating column (C), and 9) a detector (D).

4. A method of analyzing trace components in a sample in the low flow gradient high performance liquid chromatography apparatus according to claim 3, the method comprising the steps of:
    capturing a target component within the column for concentrating components (M) from a mobile phase supplied by the pump (P1);
    switching the switching valve (V); and
    feeding a mobile phase to the split tubing apparatus (ST) followed by the solvent mixing device (MC) by the pump (P2),
    wherein the target component is eluted from the separating column (C) according to an arbitrary gradient-elution linear line or curve.

5. A low flow gradient high performance liquid chromatography apparatus comprising:
    a line of components connected so a first mobile phase enters said components in the following order; 1) a pump (P1), 2) an injector (I), 3) a switching valve (V), 4) a column for concentrating components (M), 5) the switching valve (V), 6) a split tubing apparatus (STM) and 7) the switching valve (V): and
    another line of components connected so a second mobile phase enters said components in the following order; 1) a pump (P2), 2) the switching valve (V), 3) said split tubing apparatus (STM), 4) the switching valve (V), 5) the column for concentrating components (M), 6) the switching valve (V), 7) a separating column (C), and 8) a detector (D)
    wherein said split tubing apparatus (STM) comprises at least one tube connected together between a solvent inlet part and a split tubing part split into a plurality of two or more tubes and at least one tube connected between the split tubing part and a solvent outlet part via a connector (X) and a connector (Y), respectively; and wherein the connector (Y), which is joined with the plurality of split tubes, has a function for sufficiently mixing solvents.

6. A method of analyzing trace components in a sample in the low flow gradient high performance liquid chromatography apparatus according to claim 5, which comprises the steps of:
    capturing a target component within the column for concentrating components (M) from the first mobile phase supplied by the pump (P1);
    switching the switching valve (V); and
    feeding the second mobile phase to said split tubing apparatus (STM) by the pump (P2),
    wherein the target component is eluted from the separating column (C) according to an arbitrary gradient-elution linear line or curve.

7. A low flow gradient high performance liquid chromatography apparatus comprising:
    a line of components connected so a first mobile phase enters said components in the following order; 1) a pump (P1), 2) an injector (I), 3) a switching valve (V), 4) a column for concentrating components (M), 5) the switching valve (V), 6) a solvent mixing device (MC), 7) a split tubing apparatus (ST) comprising a solvent inlet partconnected by at least one tube to a split tubing part split into a plurality of two or more tubes, and a solvent outlet part connected by at least one tube to the split tubing part split into a plurality of two or more tubes; and 8) the switching valve (V) so that both the split tubing apparatus and the solvent mixing device can be filled with the first mobile phase: and another line of components connected so a second mobile phase enters said components in the following order; 1) a pump (P2), 2) the switching valve (V), 3) the split tubing apparatus (ST), 4) the solvent mixing device (MC), 5) the switching valve (V), 6) the column for concentrating components (M), 7) the switching valve (V), 8) a separating column (C), 9) and a detector (D).

8. A low flow gradient high performance liquid chromatography apparatus comprising: a line of components connected so a first mobile phase enters said components in the following order; 1) a pump (P1), 2) an injector (I), 3) a switching valve (V), 4) a column for concentrating components (M), 5) the switching valve (V), 6) a split tubing apparatus (STM) comprising at least one tube connected together between a solvent inlet part and a split tubing part split into a plurality of two or more tubes and at least one tube connected between the split tubing part split into a plurality of two or more tubes and a solvent outlet part via a connector (X) and a connector (Y), respectively; and 7) the switching valve (V); wherein the connector (Y), which is joined with the plurality of split tubes has a function for sufficiently mixing solvents: and another line of components connected so a second mobile phase enters said components in the following order; 1) a pump (P2), 2) the switching valve (V), 3) the split tubing apparatus (STM), 4) the switching valve (V), 5) the column for concentrating components (M), 6) the switching valve (V), 7) a separating column (C), and 8) a detector (D).

9. A low flow gradient high performance liquid chromatography apparatus, which comprises:

a separation column and a pump (P) for feeding a mobile phase into a split tubing apparatus; wherein said split tubing apparatus comprises a solvent inlet part;

a split tubing part split into a plurality of two or more tubes;

a solvent outlet part;

a connector (X); and a connector (Y), wherein at least one tube is connected together between the solvent inlet part and the split tubing part split into a plurality of two or more tubes via the connector (X) and wherein the split tubing part split into a plurality of two or more tubes is connected to the connector (Y) and wherein at least one tube is connected together between the connector (Y) and the solvent outlet part;

wherein said low flow gradient high performance liquid chromatography apparatus is capable of eluting a target component from said separation column according to an arbitrary gradient-elution linear line or curve by feeding a mobile phase with a different composition, and wherein the solvent outlet part is connected by a tube to a solvent mixing device thereby allowing a mobile phase discharged from the tube of the solvent outlet part to flow into the solvent mixing device.

10. The low flow gradient high performance liquid chromatography apparatus according to claim 9, wherein said split tubing apparatus further comprises a plurality of tubes each having the same or different length and/or internal diameter.

11. A method of eluting a sample comprising:

feeding a mobile phase into a split tubing apparatus followed by a separation column; wherein said split tubing apparatus comprises a solvent inlet part;

a split tubing part split into a plurality of two or more tubes;

a solvent outlet part;

a connector (X); and a connector (Y), wherein at least one tube is connected together between the solvent inlet part and the split tubing part split into a plurality of two or more tubes via the connector (X) and wherein the split tubing part split into a plurality of two or more tubes is connected to the connector (Y) and wherein at least one tube is connected together between the connector (Y) and the solvent outlet part;

eluting a target component from said separation column according to an arbitrary gradient-elution linear line or curve by feeding a mobile phase with a different composition, and flowing a mobile phase discharged from the tube of the solvent outlet part into a solvent mixing device.

12. The method of eluting a sample according to claim 11, wherein said split tubing apparatus further comprises a plurality of tubes each having the same or different length and/or internal diameter.

13. A method of analyzing components being present in trace amounts, which comprises the steps of:

feeding a mobile phase into a split tubing apparatus followed by a separation column by a pump (P); wherein said split tubing apparatus comprises a solvent inlet part;

a split tubing part split into a plurality of two or more tubes;

a solvent outlet part;

a connector (X); and a connector (Y), wherein at least one tube is connected together between the solvent inlet part and the split tubing part split into a plurality of two or more tubes via the connector (X) and wherein the split tubing part split into a plurality of two or more tubes is connected to connector (Y) and wherein at least one tube is connected together between connector (Y) and the solvent outlet part;

sequentially filling the solvent inlet part, the split tubing part split into a plurality of two or more tubes, and the solvent outlet part with the mobile phase;

eluting a target component from a separation column according to an arbitrary gradient-elution linear line or curve by feeding a mobile phase with a different composition, and flowing a mobile phase discharged from the tube of the solvent outlet part into a solvent mixing device.

14. The method of analyzing components being present in trace amounts according to claim 13, wherein said split tubing apparatus further comprises a plurality of tubes each having the same or different length and/or internal diameter.

15. A method of analyzing components being present in trace amounts in a sample with a low flow gradient high performance liquid chromatography apparatus, wherein said low flow gradient high performance liquid chromatography apparatus comprises:

a line of components connected so a first mobile phase enters said components in the following order; 1) a pump (P1), 2) an injector (I), 3) a switching valve (V), 4) a column for concentrating components (M), 5) the switching valve (V), 6) a solvent mixing device (MC), 7) a split tubing apparatus (ST), and 8) the switching valve (V): and another line of components connected so a second mobile phase enters said components in the following order; 1) a pump (P2), 2) the switching valve (V), 3) said split tubing apparatus (ST), 4) the solvent mixing device (MC), 5) the switching valve (V), 6) the column for concentrating components (M), 7) the switching valve (V), 8) a separating column (C), and 9) a detector (D):

wherein said method comprises the steps of:
feeding a first mobile phase from the pump (P1);
injecting a solution of the sample from the injector (I);
supplying the sample to the column for concentrating components (M) while diluting the sample with the first mobile phase, so that a target component in the sample is captured in the column for concentrating components (M);
switching the valve (V);
discharging the second mobile phase from the pump (P2) to the split tubing apparatus (ST), the solvent mixing device (MC), the column for concentrating components (M), the separating column (C), and the detector (D);
wherein the first mobile phase and the second mobile phase are mixed in the split tubing apparatus (ST) and form a step gradient and as the mixture of the first and second mobile phases pass through the mixing device (MC), the gradient becomes linear or linear-like to release the captured target component from the column for concentrating components (M) so that a sample band including the released target component is introduced in the separating column (C);
wherein said split tubing apparatus (ST) comprises solvent inlet part,
a split tubing part split into a plurality of two or more tubes,
a solvent outlet part,
a connector (X), and
a connector (Y)
wherein at least one tube is connected together between the solvent inlet part and the split tubing part split into a plurality of two or more tubes via the connector (X) and wherein the split tubing part split into a plurality of two or more tubes are connected to connector (Y) and wherein at least one tube is connected together between connector (Y) and the solvent outlet part.

16. A method of analyzing components being present in trace amounts in a sample with a low flow gradient high performance liquid chromatography apparatus, wherein said low flow gradient high performance liquid chromatography apparatus comprises:

a line of components connected so a first mobile phase enters said components in the following order; 1) a pump (P1), 2) an injector (I), 3) a switching valve (V), 4) a column for concentrating components (M), 5) the switching valve (V), 6) a split tubing apparatus (STM) and 7) the switching valve (V): and another line of components connected so a second mobile phase enters said components in the following order; 1) a pump (P2), 2) the switching valve (V), 3) said split tubing apparatus (STM), 4) the switching valve (V), 5) the column for concentrating components (M), 6) the switching valve (V), 7) a separating column (C), and 8) a detector (D):

wherein said method comprises the steps of:
feeding a first mobile phase from the pump (P1);
injecting a solution of the sample from the injector (I);
supplying the sample to the column for concentrating components (M) while diluting the sample with the first mobile phase, so that a target component in the sample is captured in the column for concentrating components (M);
switching the valve (V);
discharging the second mobile phase from the pump (P2) to the split tubing apparatus (STM), the column for concentrating components (M), the separating column (C), and the detector (D);
wherein the first mobile phase and the second mobile phase are mixed in the split tubing apparatus (STM) and form a linear or linear-like gradient to release the captured target component from the column for concentrating components (M) so that a sample band including the released target component is introduced in the separating column (C);
wherein the second mobile phase flows through the split tubing apparatus (STM) in an opposite direction to that of the sample;
wherein said split tubing apparatus (STM) comprises at least one tube connected together between a solvent inlet part and a split tubing part split into a plurality of two or more tubes and at least one tube connected between the split tubing part and a solvent outlet part via a connector (X) and a connector (Y), respectively, and wherein the connector (Y), which is joined with the plurality of split tubes has a function for sufficiently mixing solvents.

* * * * *